United States Patent [19]

Yamanishi

[11] Patent Number: 5,696,595
[45] Date of Patent: Dec. 9, 1997

US005696595A

[54] IMAGE FORMING APPARATUS WITH AUTOMATIC DENSITY ADJUSTMENT

[75] Inventor: Eiichi Yamanishi, Yokohama, Japan

[73] Assignee: Kabushiki Kaisha Toshiba, Kawasaki, Japan

[21] Appl. No.: 570,552

[22] Filed: Dec. 11, 1995

[30] Foreign Application Priority Data

Dec. 21, 1994 [JP] Japan .................. 6-318496

[51] Int. Cl.$^6$ .................. G01N 21/55; G03G 13/06
[52] U.S. Cl. .................. 358/298; 382/168
[58] Field of Search .................. 358/298, 455.6, 358/465.6, 475.6; 382/168–172; 399/46

[56] References Cited

U.S. PATENT DOCUMENTS

| | | | |
|---|---|---|---|
| 5,075,788 | 12/1991 | Funada | 358/458 |
| 5,351,313 | 9/1994 | Bessho et al. | 382/51 |
| 5,383,032 | 1/1995 | Euguchi et al. | 358/448 |
| 5,467,196 | 11/1995 | Fukushima et al. | 358/298 |
| 5,471,319 | 11/1995 | Ogawa | 358/445 |
| 5,502,776 | 3/1996 | Manabe | 382/172 |
| 5,585,927 | 12/1996 | Fukui et al. | 358/298 |

FOREIGN PATENT DOCUMENTS

| | | | |
|---|---|---|---|
| 3-030143 | 4/1991 | Japan . | |
| 2086077 | 8/1981 | United Kingdom | 358/298 |

*Primary Examiner*—Peter S. Wong
*Assistant Examiner*—Gregory J. Toatley, Jr.
*Attorney, Agent, or Firm*—Foley & Lardner

[57] ABSTRACT

A histogram preparation circuit prepares a density histogram from image data sent from a scanner. A histogram clear discriminating section detects a white peak of the histogram and a black peak thereof, and compares density of the white peak and that of the black peak with a white side threshold value and a black side threshold value, respectively. When the density of the white peak is the white side rather than the white side threshold value or the density of the black peak is the black side rather than the black side threshold value, it is detected whether or not a sum of the frequencies around the density of the white or black peak is a predetermined value or more. When the sum of the frequencies is the predetermined value or more, a histogram value stored in a histogram preparation circuit is cleared. A histogram is prepared by use of only image data showing the document, so that a suitable automatic density adjustment can be executed.

12 Claims, 13 Drawing Sheets

| DIVISION NUMBER | RANGE OF DENSITY OF PIXEL |
|---|---|
| 0 | 0 ~ F |
| 1 | 10 ~ 1F |
| 2 | 20 ~ 2F |
| 3 | 30 ~ 3F |
| 4 | 40 ~ 4F |
| 5 | 50 ~ 5F |
| 6 | 60 ~ 6F |
| 7 | 70 ~ 7F |
| 8 | 80 ~ 8F |
| 9 | 90 ~ 9F |
| A | A0 ~ AF |
| B | B0 ~ BF |
| C | C0 ~ CF |
| D | D0 ~ DF |
| E | E0 ~ EF |
| F | F0 ~ FF |

| NUMBER OF LINES | $a$ |
|---|---|
| 1 | 1 |
| 2 | 1/2 |
| 3 | 1/2 |
| 4 | 1/4 |
| 5 | 1/4 |
| 6 | 1/4 |
| 7 | 1/4 |
| 8 | 1/8 |
| ⋮ | ⋮ |
| 16 | 1/16 |
| ⋮ | ⋮ |
| 32 | 1/32 |
| ⋮ | ⋮ |
| 4096 | 1/4096 |
| ⋮ | ⋮ |
| 8192 | 1/8192 |

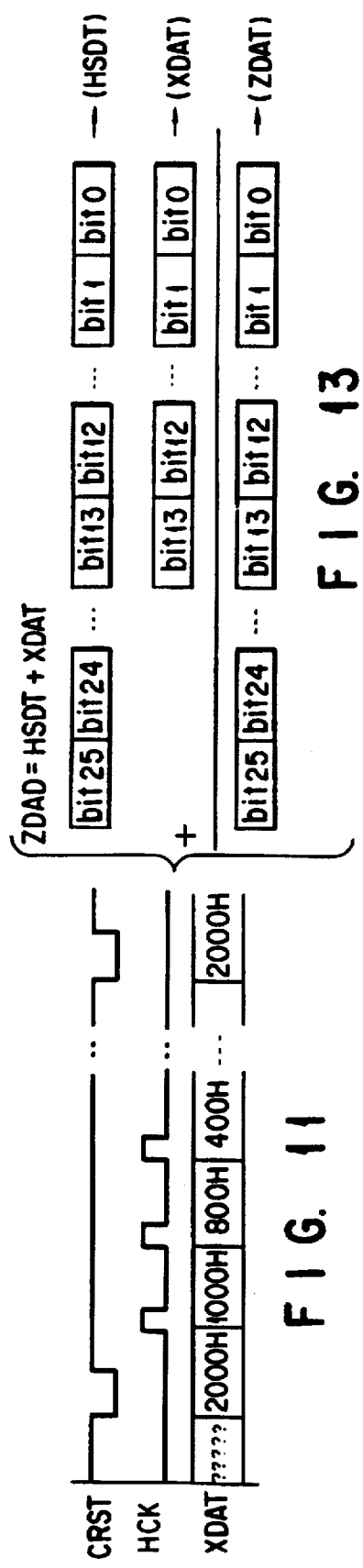

IMAGE FORMING APPARATUS WITH AUTOMATIC DENSITY ADJUSTMENT

BACKGROUND OF THE INVENTION

1. Field of the Invention

The present invention relates to an image forming apparatus such as a digital copy machine for obtaining a suitable image using a histogram based on density.

2. Description of the Related Art

In recent years, a digital image forming apparatus such as an electronic copy machine has been widely used in addition to the conventional analog image forming apparatus. Under such a circumstance, there has been tried to realize an automatic exposing function, which is the general function in the analog copy machine, in the digital copy machine. More specifically, the automatic exposing function is the function in which a density of a document is detected by a sensor and illumination of an exposure lamp is varied so as to obtain an image having a suitable quality. There is proposed a digital copy machine in which an automatic density adjustment is performed by use of a density histogram, as in Japanese Patent Application KOKOKU Publication Nos. 64-6588 and 3-30143.

In the automatic density adjustment of the digital copy machine using the histogram, since a reference value for correcting the density of the image from a numeral value of the histogram, a suitable reference value for correction can not be calculated unless the histogram correctly shows a density distribution on the document. Therefore, there occurs a problem in which the automatic density adjustment cannot be performed, or a defective image is outputted.

For example, as shown in FIG. 18, in a case where the document is placed on a document glass 92 without being come into contact with a document scale 91, and a document cover is opened, a portion (x portion) other than the document is read as an entire black portion. Due to this, black portion data is stored on the histogram, and a suitable reference value for correction cannot be obtained.

As an another example, in a case where the document is not placed at an appropriate position even if the document cover closed, a white portion of the document cover is accumulated on the histogram. Therefore, in a case where paper having a base color like a newspaper is used as a document, the automatic density adjustment cannot be suitably performed.

As mentioned above, in the conventional image forming apparatus such as a digital copy machine which performs the automatic density adjustment by use of the histogram, the entire black portion other than the document or the white portion on the document cover are reflected on the accumulative histogram. Due to this, there was a problem in which a prepared histogram does not correctly show the density distribution on the document and a suitable automatic density adjustment cannot be performed.

SUMMARY OF THE INVENTION

An object of the present invention is to provide an image forming apparatus in which a histogram on a portion other than a document is canceled to prepare a suitable histogram, and an automatic density adjustment can be performed by use of a suitable correction reference value.

In order to achieve the above object, according to the present invention, there is provided an image forming apparatus comprising: a document plate for mounting a document thereon; reading means for reading an image of a reading area of the document plate every predetermined area as moving along a scanning direction so as to output a density signal for each pixel; first preparing means for preparing a density distribution of each of the predetermined areas from the density signal output from the reading means; discriminating means for discriminating whether or not the predetermined area corresponds to the document from the density distribution prepared by the first preparing means; second preparing means for accumulatively calculating data of the density distribution prepared by the first preparing means in accordance with the movement of the reading means along the scanning direction so as to prepare a density distribution of data; correction reference value calculating means for calculating a density correction reference value of each of the predetermined areas based on the density distribution of each of the predetermined areas prepared by the first preparing means when the discriminating means discriminates that the predetermined area does not correspond to the document, and for calculating a density correction reference value of each of the predetermined areas based on the density distribution of each of the predetermined areas prepared by the second preparing means without accumulating density distribution data of the first preparing means of an area discriminated as an area where the reading means does not read the document when the discriminating means discriminates that the reading means reads the document; and image forming means for correcting the density signal output from the reading means based on the density correction reference value calculated by the correction reference value calculating means so as to form an image by use of the corrected density signal.

The above discriminating means detects a frequency peak of the density distribution of each of the predetermined areas prepared by the first preparing means so as to discriminate whether the density of the frequency peak is a black side rather than a black side threshold value or a white side rather than a white side threshold value. The above clearing means sums the frequencies around the density of the frequency peak when the density of the frequency peak is the black side rather than the black side threshold value or the density of the frequency peak is the white side rather than the white side threshold value so as to clean the density distribution prepared by the first preparing means when the summed value is larger than a predetermined value.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention and, together with the general description given above and the detailed description of the preferred embodiments given below, serve to explain the principles of the invention.

FIG. 11 is a view showing an example of an output of an addition value generating section;

FIG. 12 is a view showing a change of each signal corresponding to a change of a signal FDAT of the histogram preparing circuit of FIG. 8;

FIG. 13 is a view showing an example of an addition of signals ZDAT of the histogram preparing circuit of FIG. 8;

DETAILED DESCRIPTION OF THE PREFERRED EMBODIMENTS

Embodiments of the present invention will be explained with reference to the drawings.

Figure 1:
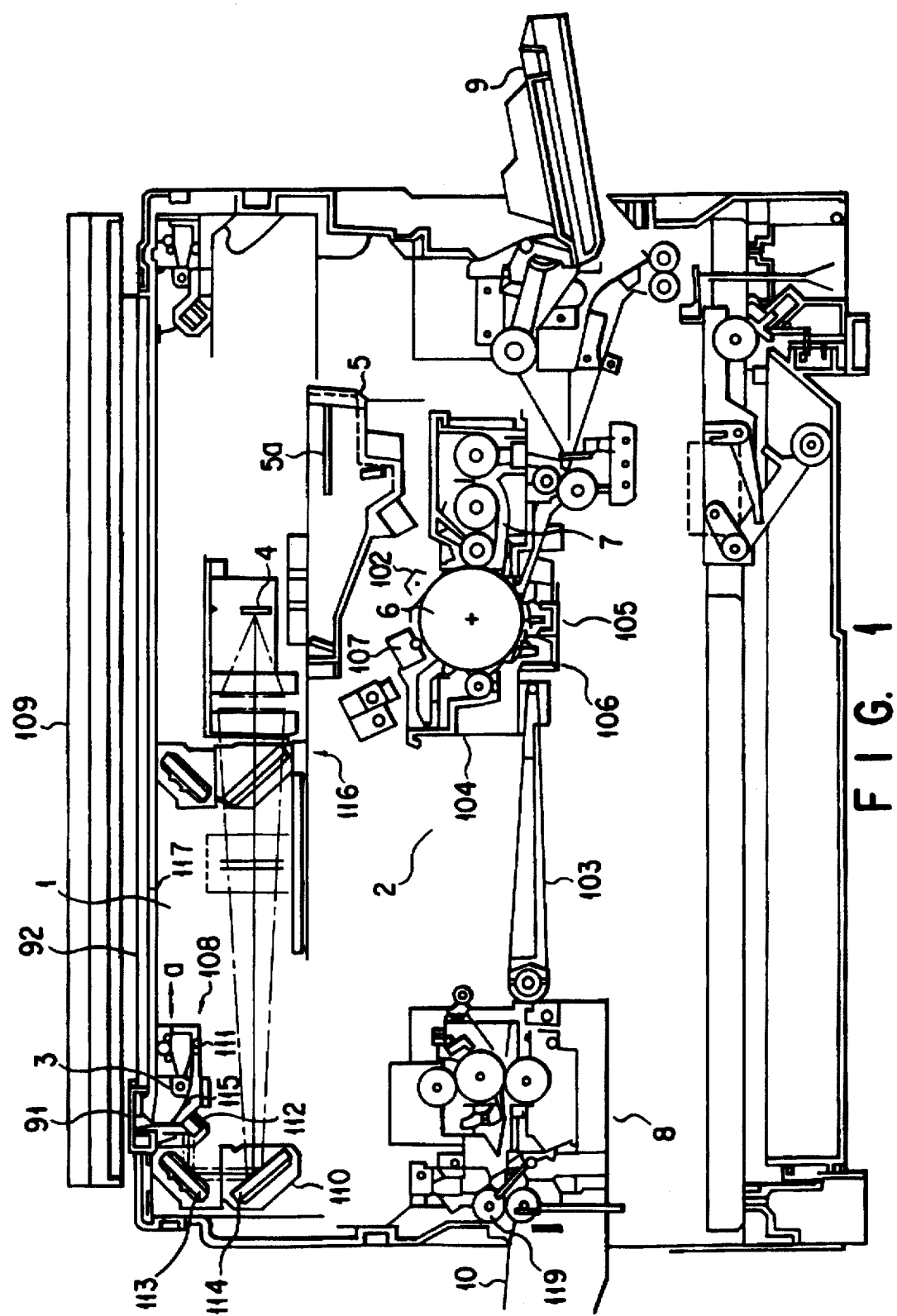
FIG. 1 is a cross sectional view showing a schematic structure of an image forming apparatus of the present invention.

FIG. 1 shows a schematic structure of an image forming apparatus to which the present invention is applied. The image forming apparatus comprises a scanner section 1 for reading a document, and a printer 2 for forming an image on paper in accordance with an image signal supplied from the scanner section 1 or an outer unit (not shown).

The scanner section 1 comprises a document plate 117 on which a document to be copied is mounted, an openable/closable document cover 109 for pressing the document mounted on the document plate 117, a fluorescent lamp 3, serving as a light source for emitting light to the document mounted on the document plate 117, and a CCD typed line sensor 4 for photoelectrically converting a reflected light from the document on which light is emitted by the fluorescent lamp 3. The fluorescent lamp 3 has a lamp heater (not shown) serving as heating means for heating a tube wall at a fixed temperature. The document plate 117 has a document scale 91 which is used such that the document is run against a document glass 92 on which the document is mounted so as to measure the position of the document.

A reflector 115 is provided on the side portion of the fluorescent lamp 3. The reflector 115 is used to efficiently converge light sent from the fluorescent lamp 3 on the document. A plurality of mirrors 112 to 114 and a lens unit 116 are provided between the fluorescent lamp 3 and the line sensor 4. The mirrors 112 to 114 are used to bend an optical path through which light directing to the line sensor 4 from the document, that is, the reflected light from the document. The lens unit 116 is used to focus the reflected light on a light receiving surface of the line sensor 4.

A scanning system comprising the fluorescent lamp 3 and the mirrors 112 to 114 are moved back and forth in a direction of an arrow a along a lower surface of the document plate 117. The document mounted on the document plate 117 is exposed and scanned at the time when the scanning system is moved back. In this case, the mirrors 113 and 114 are moved at a half speed of the mirror 112 to maintain a length of the optical path.

The reflected light, which is sent from the document by the scanning of the above scanning system, that is, the reflected light from the document on which light emitted by the fluorescent lamp 3, is reflected by the mirrors 112 to 114. Thereafter, the reflected light is passed through the lens unit 116 to be guided to the line sensor 4, so that an image of the document is image-formed on the receiving surface of the line sensor 4.

A scanning unit 108 comprises the fluorescent lamp 3, the line sensor 4, the mirrors 112 to 114, and the lens unit 116. The fluorescent lamp 3, the reflector 115, and the mirror 112 are provided at a first carriage 111, and the mirrors 113 and 114 are provided at a second carriage 110. These carriages 111 and 110 are moved by a motor (not shown), respectively.

The printer section 2 has a photosensitive drum 6, which is cylindrically shaped, and serves as an image carrier member. The photosensitive drum 6 is structured to be rotatable in a predetermined direction by a motor (not shown). The drum 6 is charged to a predetermined voltage. Also, the drum 6 is irradiated with a light beam, which is modulated in accordance with print data, thereby an electrostatic image is formed thereon.

A charging device 102, a laser unit 5, a developer 7, a transferring device 105, and a separating device 106 are provided around the photosensitive drum 6. The charging device 102 charges the surface of the photosensitive drum 6. The laser unit 5 outputs a laser beam, which is modulated in accordance with print data serving as image data to be copied or outputted onto the surface of the photosensitive drum 6. The developer 7 develops the electrostatic image, which is formed on the photosensitive drum 6 with the light beam from the laser unit 5, by adhering toner to the electrostatic image. The transferring device 105 transfers a developed toner image, which is formed on the photosensitive drum 6, to paper supplied from a paper supply section 9 to be described later. The separating device 106 separates paper absorbed on the photosensitive drum 6.

A cleaner unit 104 and an erasing device 107 are provided in order at a portion, which is the surroundings of the photosensitive drum 6 and a lower side of the separating device 106. The cleaner unit 104 cleans toner left on the surface of the photosensitive drum 6. The erasing device 107 erases the potential charged on the photosensitive drum 6 in order to form a next image.

The paper supply section 9 is provided between the developing device 7 and the transferring device 5. Paper, to which the toner image formed on the photosensitive drum 6 is transferred, is supplied to a portion between the photosensitive drum 6 and the transferring device 105 by the paper supply section 9.

In a direction where paper to which the toner image is transferred is separated from the drum 6 by the separating device 106, a fixing device 8 and a delivering device 103 are provided. The fixing device 8 fixes the toner image onto paper. The delivering device 103 delivers paper separated by the separating device 106 to the fixing device 8. Paper to which the toner image is fixed by the fixing device 8 is discharged to a discharging tray 10 by a discharging roller 119.

Figure 2:
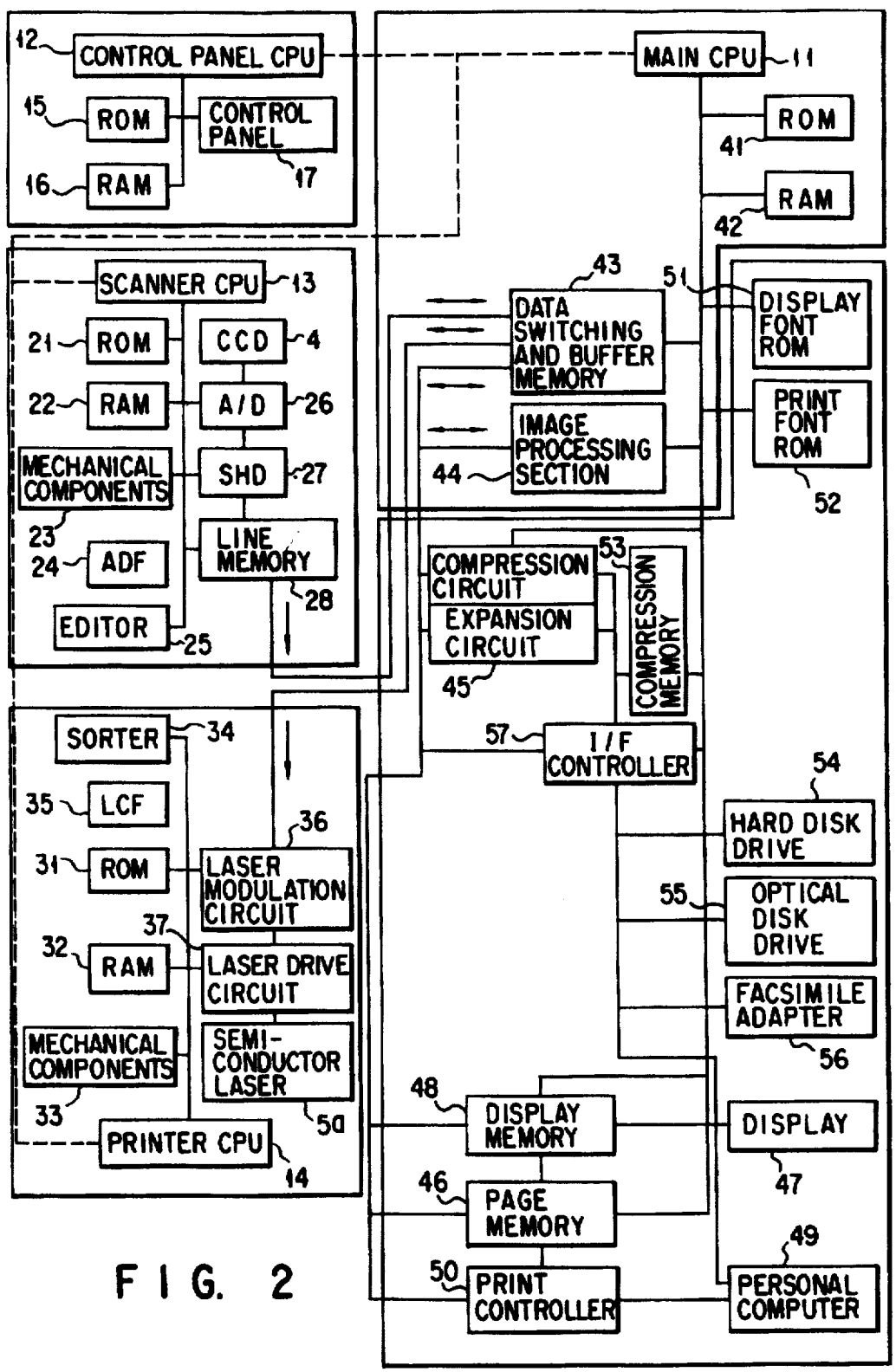
FIG. 2 is a block diagram showing a schematic structure of a controlling system of the image forming apparatus of the present invention.

FIG. 2 is a block diagram showing a schematic structure of the control system of the image forming apparatus. The apparatus is controlled by a main CPU 11, a control panel CPU 12, a scanner CPU 13, and a printer CPU 14. The main CPU 11 communicates with the control panel CPU 12, the scanner CPU 13 and the printer CPU 14 to control these CPUs.

The control panel CPU 12 is connected to a ROM 15 and a RAM 16. The control panel CPU 12 detects a switch formed on the control panel 17, turns on/off an LED, and controls a display based on data stored in the ROM 15 and the RAM 16. The scanner CPU 13 is controlled by the communication with the main CPU 11. The scanner CPU 13 controls mechanical components 23 such as a motor (not shown), and a solenoid, etc., an ADF (automatic document feeder) 24, an editor 25, an A/D (analog to digital) converter 26, an SHD (shading correcting circuit) 27, and a line memory 28.

The printer CPU 14 is controlled by the communication 2 with the main. CPU 11. The printer CPU 14 controls mechanical components 33 such as a motor (not shown), a solenoid, etc., a sorter 34, an LCF (large cassette feeder) 35, a laser modulation circuit 36, and a laser drive circuit 37 based on data stored in a ROM 31 and a RAM 32.

The main CPU 11 totally controls the image forming apparatus in accordance with a control program stored in a ROM 41 and a RAM 42. A data change and buffer memory 43 changes and buffers where data read by the scanner section 1 should be sent and which data should be sent to the printer section 2. In an image processing section 44, there are provided a circuit for preparing a histogram from image data so as to correct image data based on the prepared histogram, and an automatic density adjusting section of the present invention. A compressing and expanding circuit 45 performs compression and expansion of image data, and a page memory circuit 46 stores image data every page. A display memory 48 stores image data to be displayed on a display 47. A printer controller 50 expands code data sent from a personal computer 49 to image data. A display font ROM 51 expands code data onto the display memory 48, a print font ROM 52 expands code data onto the page memory 46, a compression memory 53 stores data compressed by the compressing and expanding circuit 45. In addition to the above-explained components, a hard disk drive 54, an optical disk drive 55, and an I/F controller 57, which carries out an interface with a facsimile adapter 56, are connected to the main CPU 11.

Figure 3:
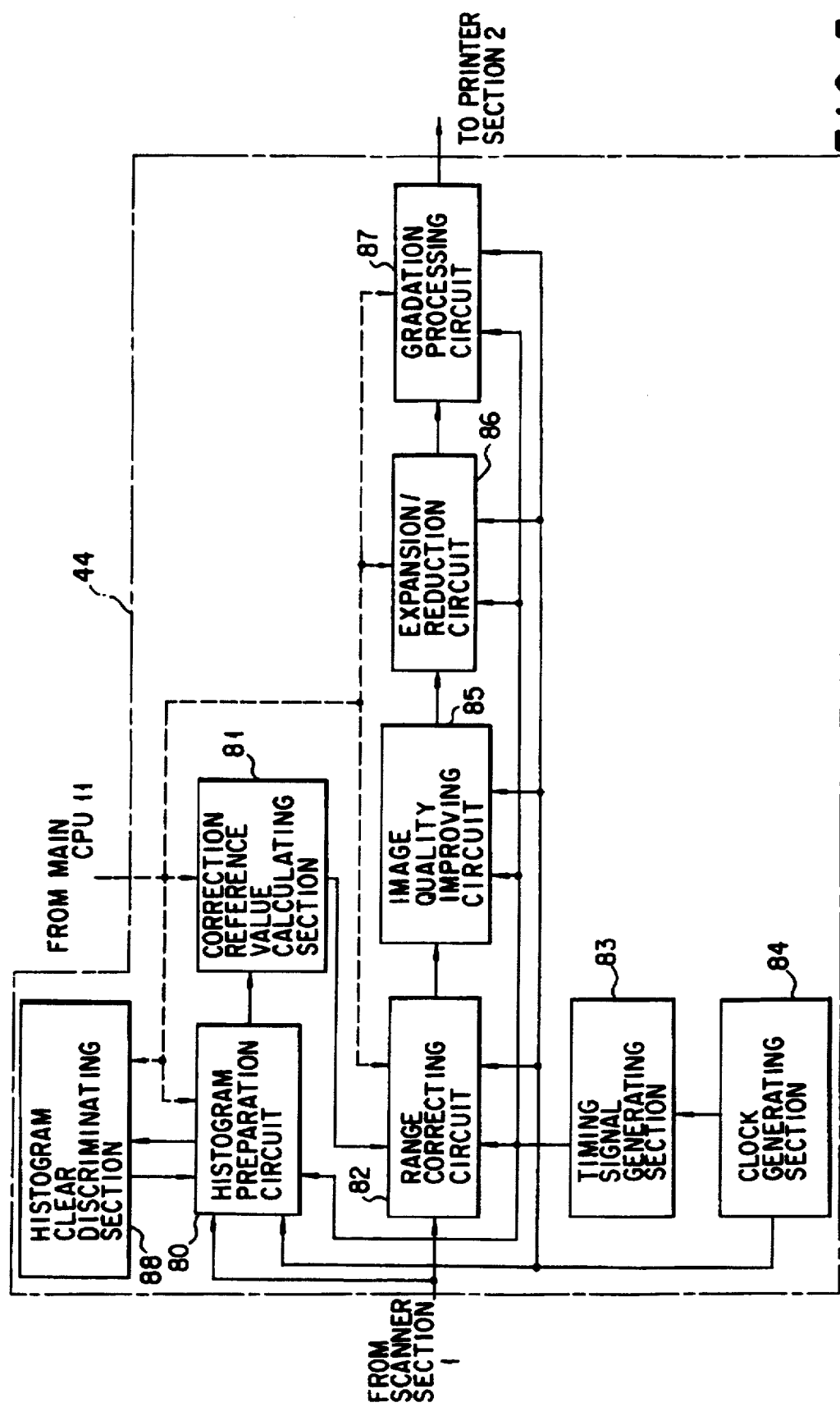
FIG. 3 is a block diagram showing a schematic structure of an image processing section of the image forming apparatus of the present invention.

FIG. 3 is a block diagram showing a schematic structure of the image processing section 44. A histogram preparation circuit 80 prepares a density histogram from image data sent from the scanner section 1. A histogram clear discriminating section 88, serving as discriminating means, discriminates whether or not the histogram prepared by the histogram preparation circuit 80 should be cleared based on a white side threshold value and a black side threshold value (to be described later), which are set by the main CPU 11.

A correction reference value calculation section 81 calculates a correction reference value (to be described later) based on the histogram prepared by the histogram preparation circuit 80. A range correction circuit 82 corrects a density range (to be described later) by use of the correction reference value from the correction reference calculation section 81 to perform the automatic density adjustment at real time.

A timing signal generating section 83 generates various timing signals necessary for each block of the image processing section 44 based on a clock signal from a clock generating section 84. An image improving circuit 85 includes a low pass filter, and a high frequency emphasizing circuit to improve the quality of the image range-corrected by the range correction circuit 82. An expansion/reduction circuit 86 expands/reduces an image as required. A gradation processing circuit 87 processes a gradation of an image by a dither method or an error diffusion method. The above processed image signal is sent to the printer section 2, and an image is formed.

FIG. 4 shows an outline of a density histogram prepared by the histogram preparation circuit 80. For example, for reading an image of one A4 paper, if the image is read at 400 dpi, the total number of pixels G is shown as follows:

$$G=210\times297\times(400/25.4)^2$$

Figures 4A, 4B, 6:
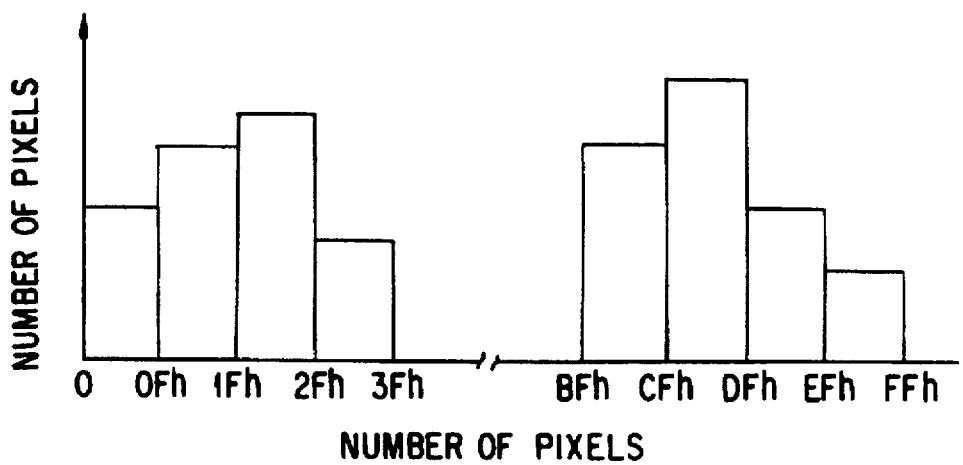
FIGS. 4A and 4B are views explaining a histogram prepared in the present invention.
FIG. 6 is a view showing a number of sub-scanning lines and their corresponding coefficient α.

Each pixel has its density, and the density is expressed by 8 bits herein. In FIG. 4A, a horizontal axis shows a density, that is, a pixel value, and a vertical axis is a frequency (number of pixels) showing how many pixels exist at each density of pixel.

As shown in FIG. 4A, according to this embodiment, the density is divided to sixteen, and the density having 256 levels is simplified to 16 levels. In other words, lower 4 bits of 8-bit pixel value are ignored. By use of 16 divisions, the hardware can be largely simplified. Even in the case of 16 divisions, an amount of data necessary for histogram can be fully reversed in the automatic density adjusting function. FIG. 4B shows a method of 16 even divisions, a division number 0 shows a range of the pixel density of 0 to F, a division number 1 shows a range of the pixel density of 10 to 1 F. Similarly, the pixel value ranges of division numbers 2 to F are set.

The following will explain the correction reference value calculation section 81 and the range correction of the range correction circuit 82. The range correction is a function, which is used in a background deletion in the automatic exposure function of the analog copy machine.

Figure 5A:
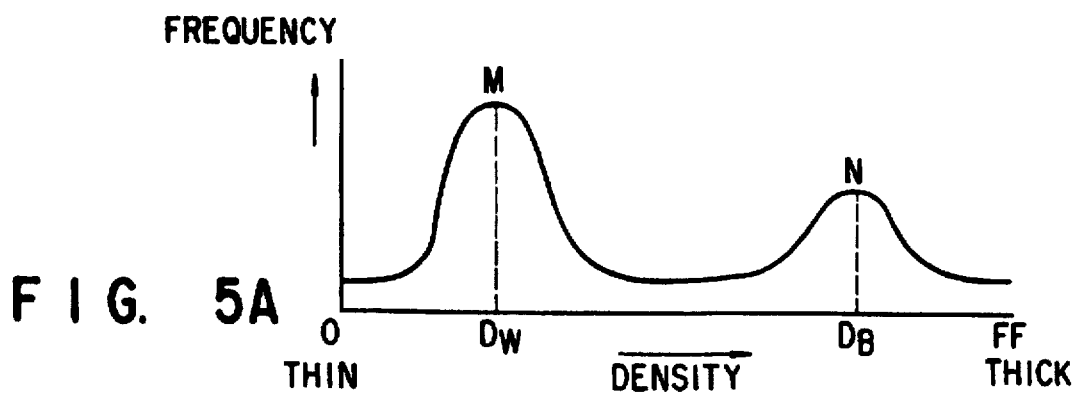
FIGS. 5A and 5B are histogram views explaining a correction reference value and a range correction.

Generally, if the document is digitally read and a density histogram is prepared, the result can be obtained as shown in FIG. 5A. In a case of the document like newspaper, one curve whose peak is M can be formed at a background density portion and one curve whose peak is N can be formed at a character density portion. In the analog copy machine, an exposure lamp is controlled such that the background density portion can be excluded. However, since the background density portion cannot be excluded in the digital copy machine, the similar effect can be obtained by the following method.

Figure 5B:
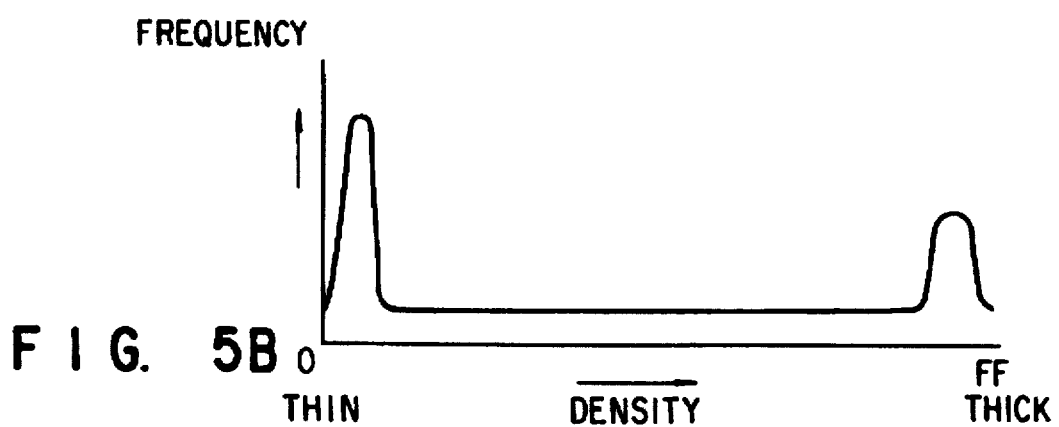

More specifically, density DW corresponding to the peak point of frequency M, and density DB corresponding to the peak point of frequency N are obtained, and the following calculation is performed, so that a density histogram is converted to a distribution as shown in FIG. 5B. The densities DW and DB are called as correction reference values, and each correction reference value is calculated by the correction reference value calculation section 81 based on the histogram of each scanning line which is prepared by the histogram preparation circuit 80.

$$DN=(DI-DW)\times FFH/(DB-DW)$$

where DI is an input pixel density, DN is a corrected pixel density, and FFH is a maximum pixel density. In other words, the range (density width) between M to N shown in FIG. 5A is expanded from 0 to FFh.

The following will explain the histogram preparation system of system of the present invention.

The following equation is a basic calculation expression for preparing the histogram of the present invention. The histogram is prepared every main scanning line. A basic reference value of the range correction is obtained every time when the histogram preparation processing is executed based on the obtained reference value. The total amount of data, which constitute the histogram, is a fixed value.

$$A'=A-\alpha A+\alpha B$$

where A': a corrected frequency (number of pixels) corresponding to each density of the present line, A: a frequency corresponding to each density calculated up to the previous line, B: a frequency corresponding to each density of the present line, and α: weighting coefficient.

The frequency value accumulated in each line is multiplied by the weighting factor α. In other words, the weighting coefficient α shows a contribution ratio to the histogram. The value of α is set in accordance with the number of lines. Thus, the value is selected from 14 values (1/power of 2), i.e., 1, 1/2, 1/4, 1/8, 1/16, 1/32, ... 1/2048, 1/4096, 1/8192 (=$1/2^{13}$).

Figure 7:
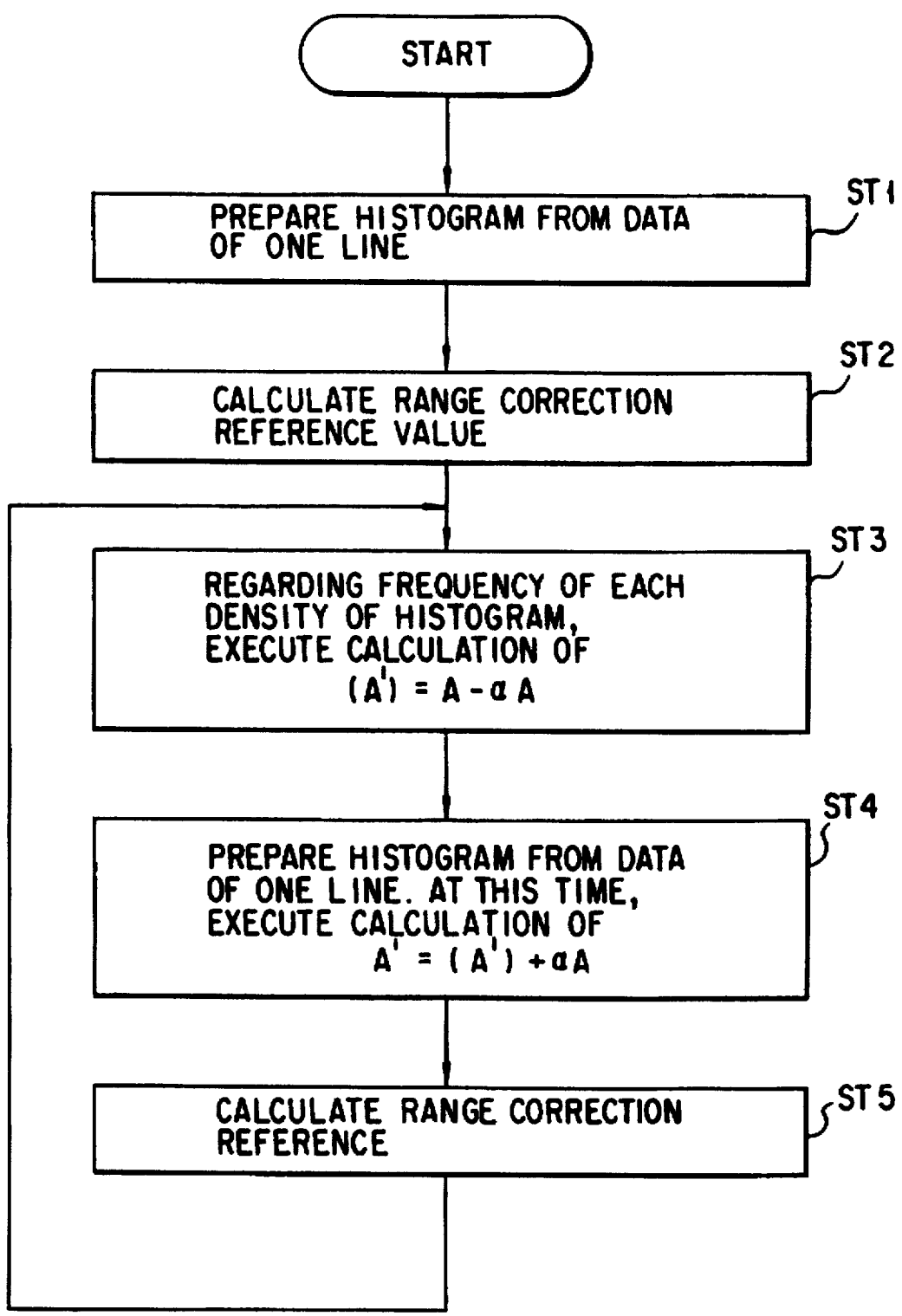
FIG. 7 is a flow chart showing an operation of a histogram preparing circuit.

FIG. 7 is a flow chart showing an operation of the histogram preparation circuit 80. The histogram preparation circuit 80 prepares a histogram from data corresponding to the first scan line (ST1). The correction reference value calculation section 81 calculates the reference value for the range correction from the histogram prepared by the histogram preparation circuit 80 (ST2). The histogram preparation circuit 80 calculates (A')=A−αA for each frequency value of densities of the histogram during the time between a line reading and next line reading, that is, when no pixel density is inputted (ST3). The histogram preparation circuit 80 calculates A'=(A')+αB for each input pixel while reading one line (ST4). In this way, the histogram preparation circuit 80 generates a corrected frequency value of the present line, A'=A−αA+αB. From the generated histogram, the reference value for a range correction is calculated by the correction reference value calculation section 81 (ST5).

In the preparation of the histogram, two modes, that is, a mode 0 and a mode 1 are set, and either one of modes is selected as required.

Mode 0: a weighting factor varied addition mode depending on the number of scanning lines; and Mode 1: a weighting factor fixed addition mode against the input pixel.

In mode 0, the value of coefficient α is varied in accordance with the number of counts of the main scanning lines to prepare the histogram. In mode 1, the coefficient is fixed, and the histogram is prepared regardless of the count value of the main scanning line.

Figure 8:
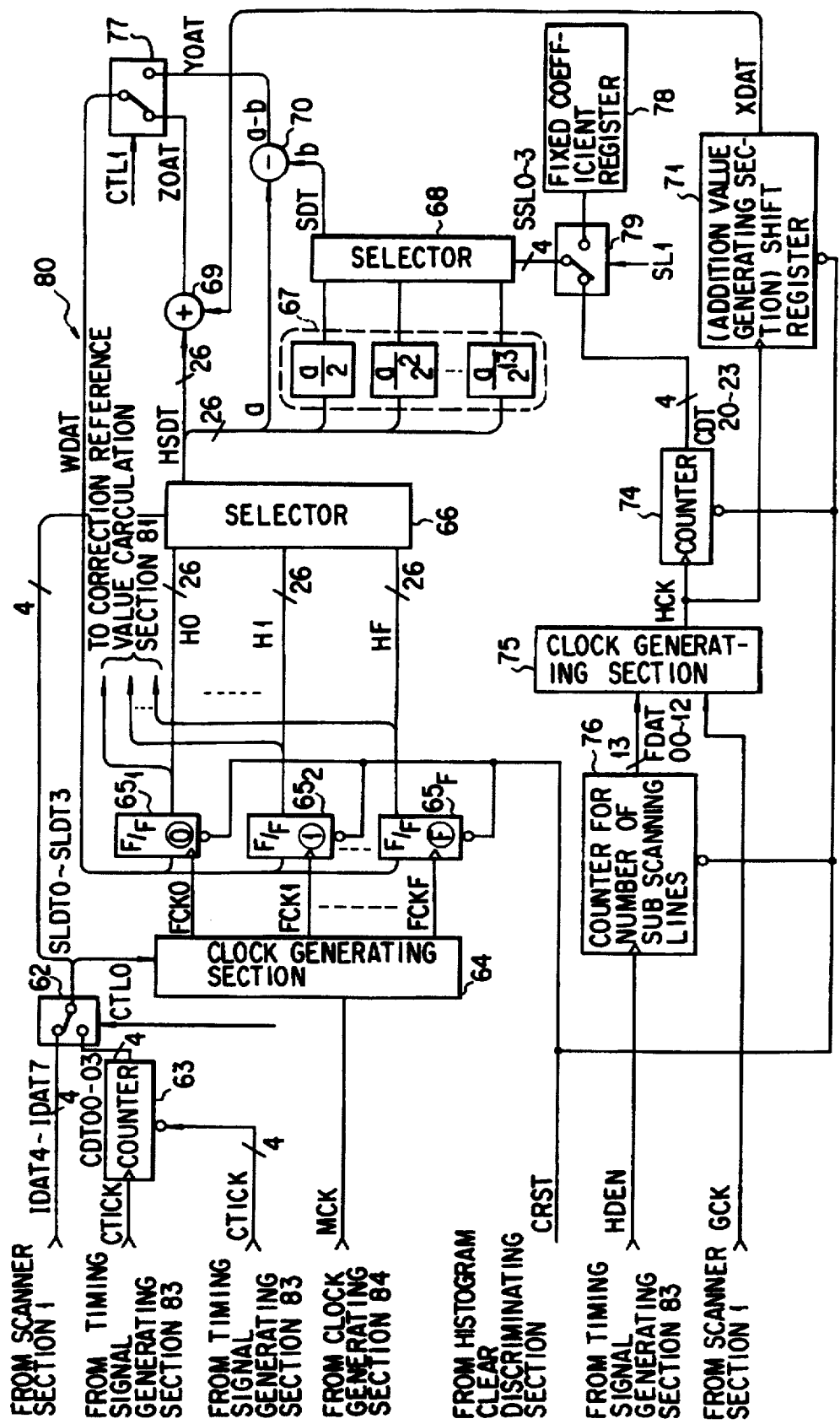
FIG. 8 is a block diagram showing a structure of the histogram preparing circuit in the image forming apparatus of one embodiment of the present invention.

FIG. 8 is a block diagram showing the specific structure of the histogram preparation circuit 80. Pixel density signals IDAT 4 to IDAT 7 are input to one terminal of a switch 61 from the scanner section 1, and output data signals CDT00 to CDT03 are input to the other terminal from a counter 63. The switch 62 selects either one of input signals in accordance with a selection signal from the timing signal generating section 83, and outputs the selected signals SLDT0 to SLDT3 to a selector 66 and a clock generating section 64.

In this case, the pixel density signals IDAT4 to IDAT7 correspond to upper 4 bits of the pixel density, and the pixel density signals IDAT0 to IDAT3 are ignored for the above-mentioned reason. The timing signal CTL0 sent from the timing signal generating section 83 is in a high level when the pixel density signal is not read, and the switch 62 selects a signal from the counter 63 to be output.

The counter 63 supplies a necessary value to the clock generating section 64 and the selector 66 in calculating (A')=A−αA. When the above-mentioned pixel density signal is not read, the counter 63 generates a four-bit count value such that sixteen outputs of the clock generation section 64 are selected and generated in order. A counter clock signal CTICK is inputted from the timing signal generating section 83, and the counter 63 is cleared by the counter clear signal CTICL from the timing signal generating section 83. The counter clear signal CTICL is in a low level when the pixel density signal is read, and the counter 63 is cleared.

Figure 9:
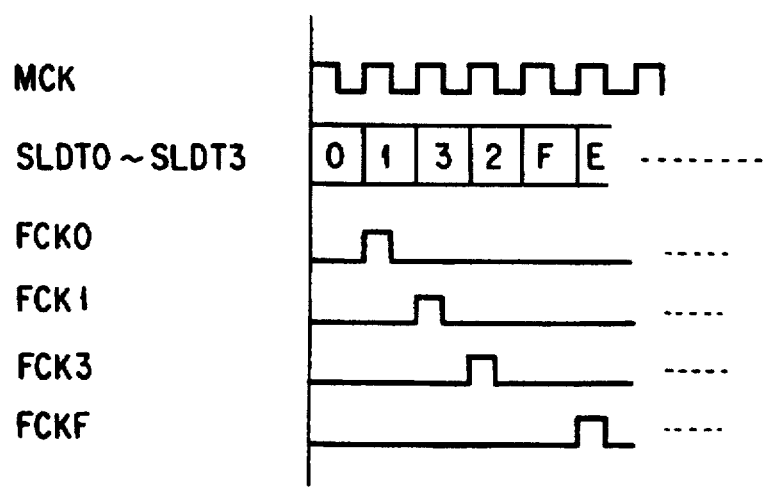
FIG. 9 is a view showing a change of each signal corresponding to a change of a signal FDAT of the histogram preparing circuit of FIG. 8.

The clock signal generating section 64 selects one of sixteen outputs FCK0 to F at a period of an input clock signal MCK to be output in accordance with the selection input signals SLDT0 to SLDT3. FIG. 9 shows the relationship between I/O signals of the clock signal generating section 64.

Histogram registers (flip-flop) $65_1$ to $65_F$ latch a corrected frequency (WDAT) against each pixel density to be output when the input clock signals FCK0 to F rise. The input signals WDAT is the above-mentioned A'−αA or (A')+αB. Corrected frequency signals H0 to HF sent from the histogram registers $65_1$ to $65_F$ are also output to the correction reference value calculation section 81.

The selector 66 inputs the frequency (the number of pixels) corresponding to each density of 16 divisions from the histogram registers $65_1$ to $65_F$, and selects one data from 16 data H0 to HF (each bus width is 26 bits) to output a signal HSDT.

Figure 10:
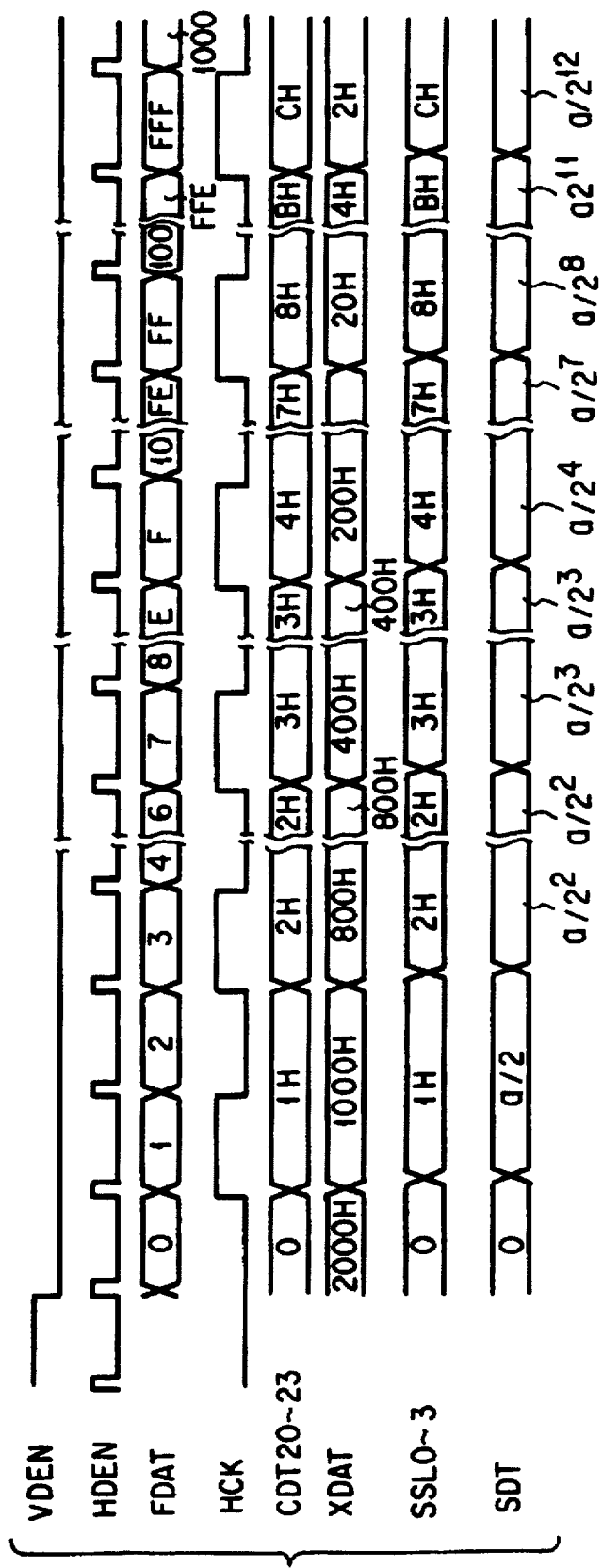
FIG. 10 shows a relationship between input and output signals of a clock generating section 64 of the histogram preparing circuit of FIG. 8.

As shown in a timing chart of FIG. 10, a sub-scanning line number counter 76 outputs a line synch signal HDEN from the timing signal generating section 83, and outputs count value signals FDAT00 FDAT12 to a clock generating section 75. Then, the counter 76 is cleared by a clear signal CRST sent from the main CPU 11 every time when one page of the document is scanned.

The clock generating section 75 inputs output signals FDAT0 to FDAT12 sent from the sub-scanning line number counter 76, and a pixel synch clock signal GCK sent from the scanner section 1, and outputs a signal HCK to a counter 74 and an addition value generating section 71. When the value of the signal FDAT is one of 1, 3, 7, F, 1 F, 3 F, 1 FF, 3 FF, 7 FF, FFF, and 1 FFF, the clock generating section 75 outputs one clock of the input pixel synch clock signal. The clock generating section 75 comprises an AND circuit. When all line number signals FDAT are "1", that is, FDAT= 1, 3 (11), 7 (111), F (1111), ..., the clock generating section 75 outputs one clock.

The counter 74 inputs the clock signal HCK from the clock generating section 75, and outputs count value signals CDT20 to CDT23 to a selector 68 when the mode is set to 0. The counter 74 is also cleared by the clear signal CRST sent from the main CPU 11 every time when one page of the document is scanned. The count values CDT20 to CDT23 are values for selecting α as shown in FIG. 6.

A fixed coefficient value register 78 outputs a fixed coefficient value when the mode is set to 1. A switch 79 is changed in accordance with a mode signal SL1 sent from the CPU 11. The switch 79 is set to the counter 74 when the mode is set to 0, and to the register 78 when the mode is set to 1.

A subtraction value generating section 67 outputs "αA" in calculating (A')=A−αA. The subtraction value generating section 67 inputs the output signal HSDT from the selector 66, and generates a value, which is obtained by dividing the signal HSDT by a power of 2 (the signal HSDT is shifted).

The selector 68 determines "αA" of the calculation (A') =A−αA, which is performed between the respective lines, that is, when the pixel signal is not read, in accordance with input signals SSL0 to SSL3. In other words, the selector 68 outputs (value of signal HSDT)/$2^2$ when the value of the input signal SSL0 is SSL3 is "1", and (value of signal HSDT/$2^{13}$ when the input value is C.

A subtraction section 70 performs a subtraction (A')=A−αA. The subtraction section 70 inputs the density signal HSDT (A of the above equation) from the selector 66 and a subtraction signal SDT (αA of the above equation) from the selector 68, and outputs a signal YDAT as a result of the subtraction.

The addition value generating section 71 (shift register) generates "αB" in calculating A'=(A')+αB. The addition value generating section 71 inputs the clock signal HCK from the clock generating section 75, and outputs a signal XDAT to an adding section 69. The addition value generating section 71 is also cleared by the clear signal CRST sent from the main CPU 11 every time when one page of the document is scanned. FIG. 11 shows an example of the output of the addition value generating section 71. At the time of inputting the clear signal CRST, an initial value output is 2000 H. Thereafter, every time when the clock signal HCK enters from the clock generating section 75, ½ of the present value 2000 H is 1000 H, and ½ of the present value 1000 H is 800 H. FIG. 12 shows a variation of each signal corresponding to the variation of the signal FDAT.

The adding section 69 carries out addition A'=(A')+αB. The adding section 69 inputs the frequency signal HSDT from the selector 66, and the signal XDAT of addition data from the addition value generating section 71, and outputs a signal ZDAT as a result of the addition. FIG. 13 shows an example of the addition of the signal ZDAT.

A switch 77 changes the calculations of (A')=A−αA and A'=(A')+αB. The addition result signal ZDAT is input to one terminal of the switch 77 from the adding section 69, and the subtraction result signal YDAT is input to the other terminal from the subtraction section 70. One of inputs is selected in accordance with a selection signal CTL1, and a selection result signal WDAT is output to the histogram registers $65_1$ to $65_F$.

The preparation of the histogram having the structure shown in FIG. 8 will be explained with reference to timing charts of FIGS. 14 and 15.

Figure 14:
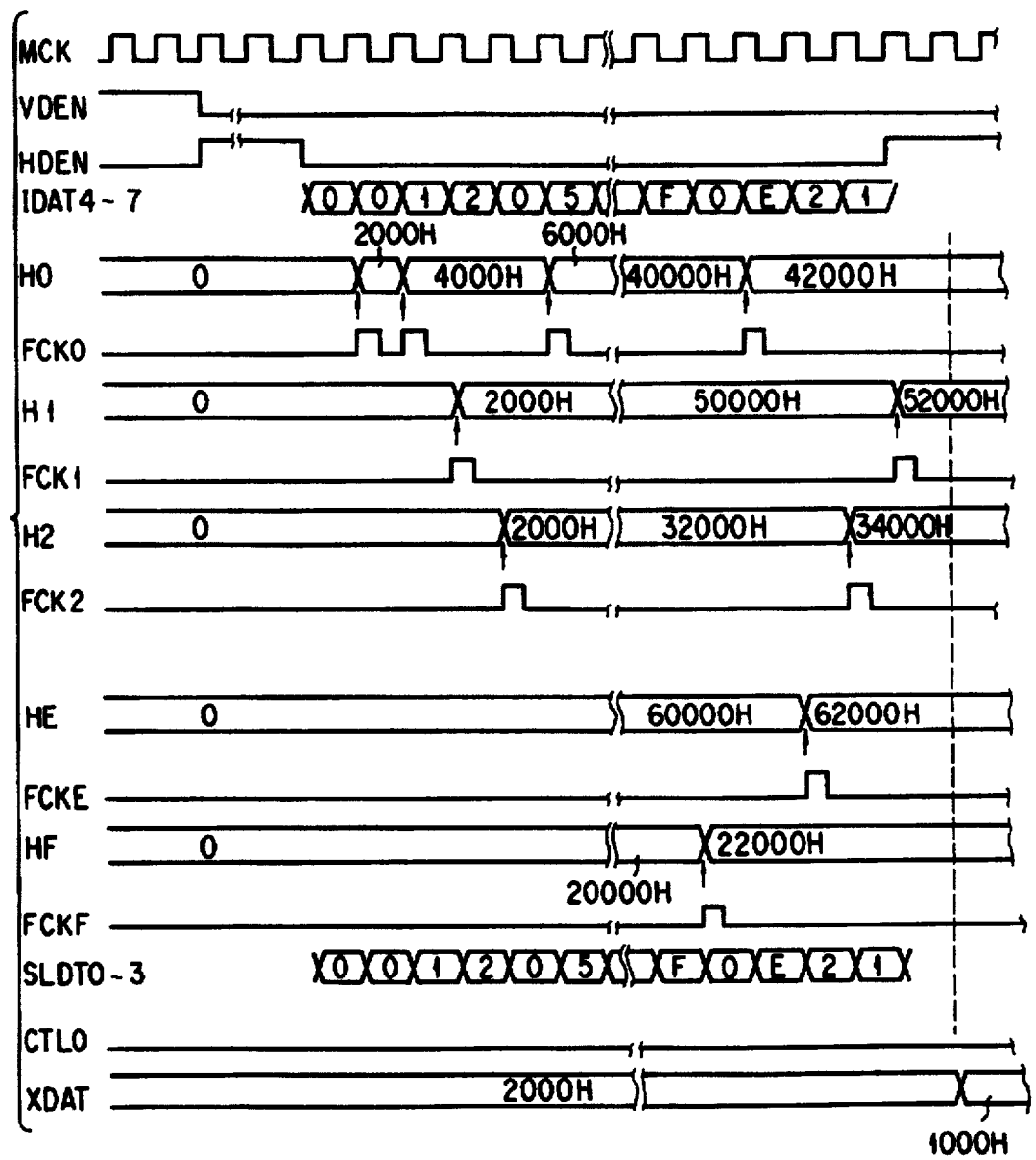
FIG. 14 is a timing chart explaining an operation of the histogram preparing circuit of FIG. 8.

FIG. 14 is a timing chart showing a state when A'=(A')+αB is calculated every input pixel during one line reading. The signal MCK is a main clock and synthesized with the pixel signal. A signal VDEN is a page synch signal, and a signal HDEN is a line synch signal. The pixel density signals IDAT4 to IDAT7 sent from the scanner section 1 are upper four bits of the pixel density, and input to the switch 62. A sub-scanning effective signal CTL0 is enable (low level) in this case. The switch 62 sends inputs IDAT4 to IDAT7 to the selector 66 and the clock generating section 64.

The selector 66 selects the output (frequency) of the histogram registers $65_1$ to $65_F$ in accordance with the pixel signals $IDAT_4$ to $IDAT_7$, that is, the value of the selection input signal, and outputs the selected frequency signal HSDT. A weighting factor (XDTA) is added to the signal HSDT in accordance with the number of liens by the adder section 69. Since the switch 77 is set to the adding section 69 by the input signal CTL1 in this case, the addition result signal ZDAT is returned to the histogram registers $65_1$ to $65_F$.

The clock generating section 64 outputs the clock signals FCK0 to FCKF in accordance with the pixel signals IDAT4 to IDAT7. Each of the histogram registers $65_1$ to $65_F$ latches, i.e., stores the value of the output signal WDAT of the switch 77 when each of the clock signals FCK0 to FCKF rises. The above-mentioned processing is provided every pixel of one line, so that the histogram of one line is generated, and the reference value for adjusting the pixel density is calculated. The reference value is used in the processing of the next line.

During the time, which is from one line reading to a next line reading, that is, when the pixel density signal is not input, the equation, (A')=A−αA, is calculated to obtain the frequency of each density of the histogram.

Figure 15:
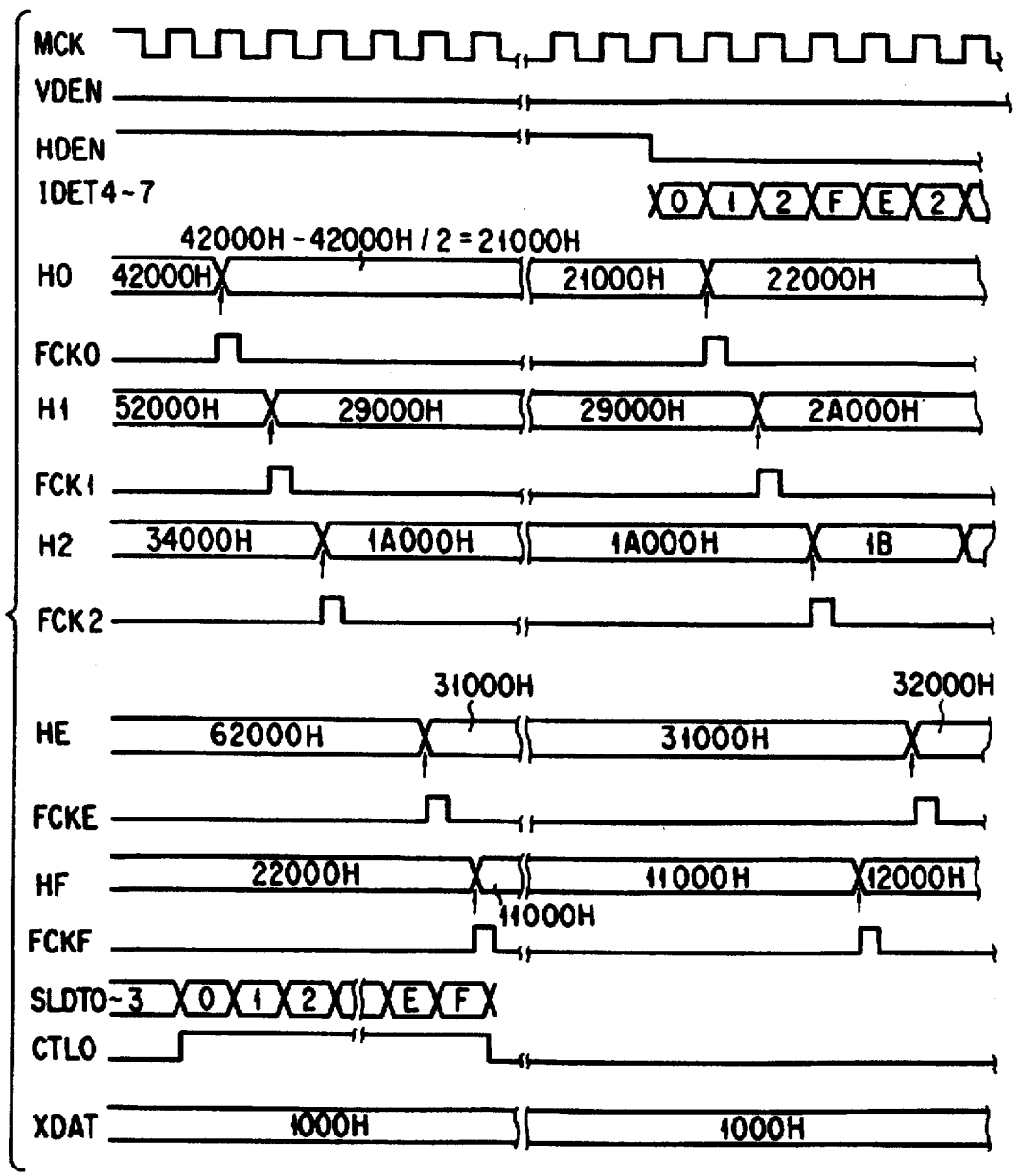
FIG. 15 is a timing chart explaining an operation of the histogram preparing circuit of FIG. 8.

FIG. 15 is a timing chart showing a state of the subtraction processing. The switch 62 is changed to the counter 63 by the selection signal CTL0, and the switch 77 is changed to the subtracter 70 by the selection signal CTL1. The selector 68 subtracts each histogram value based on the coefficient (in mode 0), which is determined by the number of sub-scanning counters, or the fixed coefficient (in mode 1). After the subtraction is ended, an operation is moved to the operation of the histogram preparation of the next line.

By repeating the above-mentioned operations, in the case where the mode is set to 0, the histogram in which total amount of data is constant is prepared every time when each main scanning line is read. In the case where the mode is set to 1 and the weighting factor is fixed, a histogram, which can deal with the sharp change of the density of the document image, can be obtained.

Figure 16:
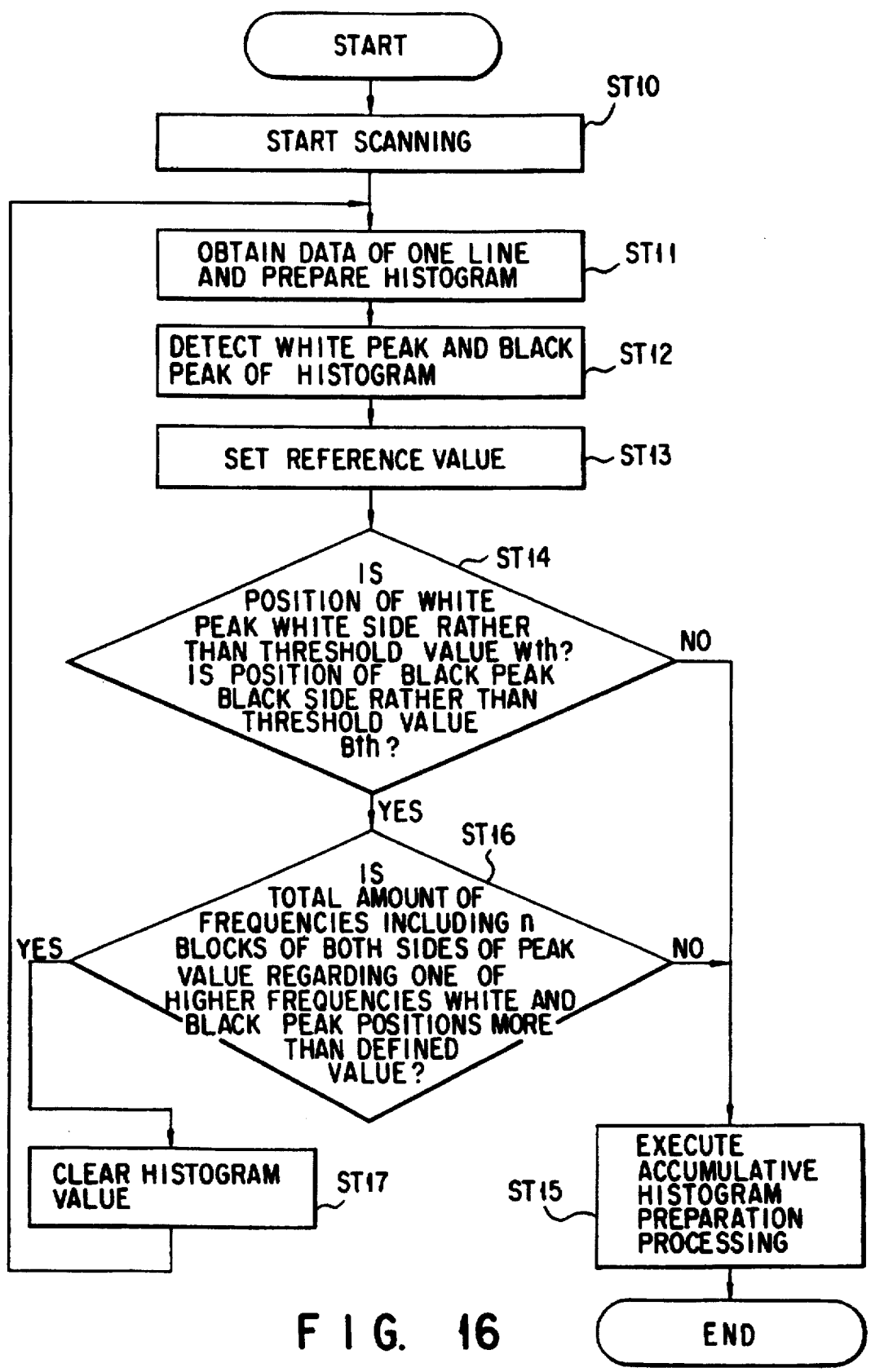
FIG. 16 is a flow chart explaining image data processing based on the histogram according to the present invention.

The following will explain the image data processing based on the histogram of the present invention with reference to a flow chart of FIG. 16. In this embodiment, it is discriminated whether or not input image data is document image data, and the histogram is prepared by use of only document image data.

First of all, image data read by the scanner section 1 is scanned to be sampled by the histogram preparation circuit 80 of the image forming processing section 44 (ST10). Then, a histogram of a first scanning line is prepared (ST11). The histogram clear discriminating section 88 discriminates the white peak and the black peak of the histogram prepared by the histogram preparation circuit 80 (ST12). The correction reference value calculation section 81 determines a reference value for a density adjustment (ST13).

Figure 17A:
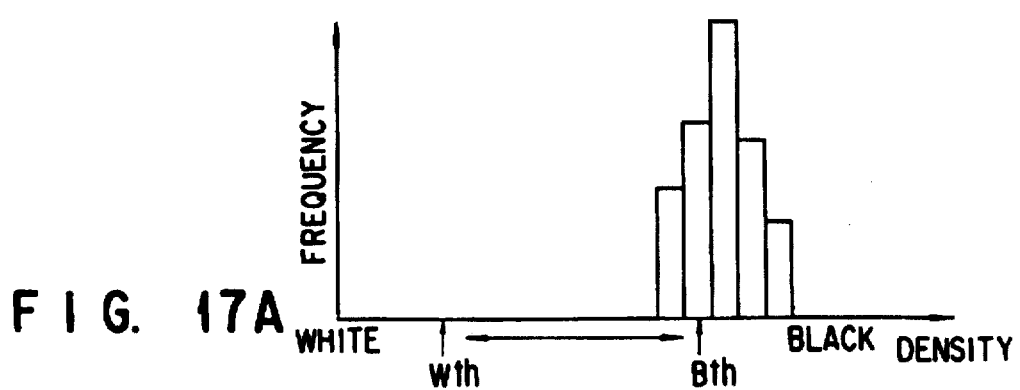
FIGS. 17A to 17C are views each showing an example of a histogram by a scanning sampling on one line.
Figure 17B:
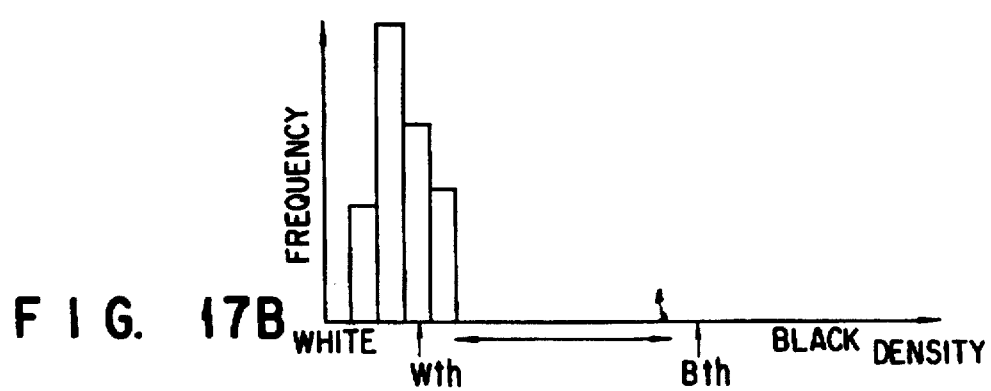
Figure 17C:
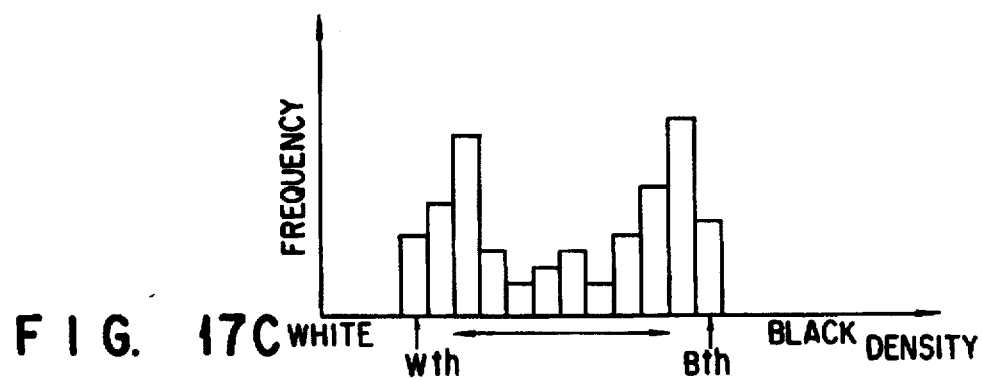
Figure 18:
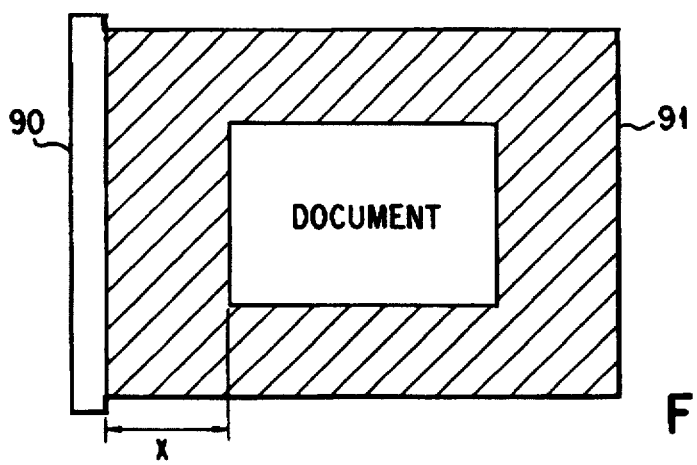
FIG. 18 is a view explaining a state where a document is placed on a document glass.

FIGS. 17A to 17C are views each showing an example of a histogram by scanning and sampling one line. FIG. 17A shows the histogram when the document cover 109 is opened and the scanner section 1 reads a non-document area, that is, an area other than the document. In this case, the peak of the histogram is one-sided to the black side (high density). FIG. 17B shows the histogram when the document cover 109 is closed and the scanner section 1 reads a white document cover. In this case, the peak of the histogram is one-sided to the white side (low density). FIG. 17C shows the histogram when the normal image (e.g., newspaper) reading is carried out.

As shown in FIGS. 17A to 17C, when the document reading and the reading of the non-document area are performed, the histogram is characteristically one-sided in their distributions. According to the present invention, the histogram whose distribution is extremely one-sided is ignored, and histograms obtained by use of only document image data are accumulated. Thereby, a suitable correction reference value is calculated, and the automatic density adjustment is performed.

In the histogram clear discriminating section 88, a white side threshold value Wth and a black side threshold Bth are set in advance. The peak (white peak) of the histogram of the white side in the histogram scan-sampled on one line is compared with the threshold value Wth, and the peak (black peak) of the histogram of the black side is compared with the threshold value Bth (ST14).

In a case of the document like newspaper shown in FIG. 4A, one curve of the histogram can be formed at a relatively thin density portion corresponding to the background portion, and one curve can be formed at a relatively thick density portion corresponding to the black character portion. Therefore, the threshold value Wth of the white side and the threshold value Bth of the black side are set in consideration of the distribution state of the histogram.

For example, as shown in FIG. 17A, in a case where the position of the black peak is placed at a black side rather than the threshold value Bth, it can be discriminated that this is not the document reading. As shown in FIG. 17B, in a case where the position of the white peak is placed at a white side rather than the threshold value Wth, it can be discriminated that this is not the document reading. In a case of FIG. 17C, since the position of the white peak is placed at a black side rather than the threshold value Wth, and the position of the black peak is placed at a white side rather than the threshold value Bth, it can be discriminated that this is the document reading.

In other words, in the case where the histogram clear discriminating section 88 discriminates that the position of the white peak is placed at the black side rather than the threshold value Wth and the position of the black peak is placed at the white side rather than the threshold value Bth, the histogram preparation circuit 80 executes the normal accumulative histogram preparation processing (ST15).

Also, in the histogram clear discriminating section 88, if the detected position of the black peak is placed at the black side rather than the threshold value Bth or the position of the white peak is placed at the white side rather than the threshold value Wth, the operation goes to the following step.

The histogram clear discriminating section 88 discriminates whether or not a sum of the frequencies of n blocks which centrally include one of higher frequencies of the white peak and the black peak, is a predetermined value Z or more (step ST16). The reason why the density of the peak frequency of only one of higher frequencies of the white peak or the black peak is counted is as follows.

More specifically, if both white peak frequency and the black peak frequency are counted, the normal character document may be included. In other words, the above method is used to omit data of the area, which can be considered to be unnecessary.

If the sum of the frequencies of n blocks is less than the predetermined value Z, the histogram preparation circuit 80 prepares the accumulative histogram by use of the histogram data. If the total amount of the frequencies of n blocks is the predetermined value Z or more, each frequency stored in the histogram preparation circuit 80 (651 to 65F) is cleared by the histogram clear discriminating section 88 (step ST17). Then, a preparation of a new histogram is executed by use of read data of a next line. In other words, in the cases of FIGS. 17A and 17B, the the histogram clear discriminating section 88 discriminates that the document is not correctly placed on the document glass 92 of the document plate 117 and that the scanner section 1 scans and samples the space between the document and the document scale 91. Therefore, the respective frequencies, which are stored in the histogram preparation circuit 80 (651 to 65 F) as a result of scanning the above space by the scanner section 1, are all cleared.

It is noted that the threshold values Wth and Bth of the histogram clear discriminating section 88 are variable by the setting of the main CPU 11. Also, the predetermined value Z for the sum of the frequencies of n blocks of the histogram clear discriminating section 88 is variable by the main CPU 11. Moreover, by the result of the various experiments, a routine for clearing the histogram is carried out when the sum is 92 to 93% or more of the total number of pixels of one line.

As mentioned above, according to the present invention, since the portion other than the document, that is, black data and white data of the non-document portion are not used as histogram data, a suitable histogram can be prepared. Therefore, the automatic density adjustment can be executed based on the suitable correction reference value.

The accompanying drawings, which are incorporated in and constitute a part of the specification, illustrate presently preferred embodiments of the invention and, together with the general description given above and the detailed description of the preferred embodiments given below, serve to explain the principles of the invention.

What is claimed is:

1. An image forming apparatus comprising:

a document plate on which a document is placed, the document plate having a plurality of reading areas;

means for reading an image in the reading area of said document plate as moving along a scanning direction so as to output a density signal for each pixel;

means for preparing a first density distribution corresponding to each reading area based on the density signal;

means for discriminating that the reading area corresponds to the document from the first density distribution;

first calculating means for accumulatively calculating data of the first density distribution in accordance with the movement of said reading means along said scanning direction so as to prepare a second density distribution;

second calculating means for calculating a density correction reference value of each of said reading areas based on the first density distribution of each of said reading areas when said discriminating means discriminates that said reading area does not correspond to the document, and for calculating a density correction reference value of each of said reading areas based on the second density distribution without accumulating the first density distribution data of the reading area discriminated as said reading area where said reading means does not read the document when said discriminating means discriminates that said reading means reads the document;

means for correcting the density signal by using the density correction reference value so as to output a corrected density signal; and means for forming an image on a image bearing member on the basis of the corrected density signal.

2. The apparatus according to claim 1, wherein said discriminating means includes means for detecting a frequency peak of the density distribution of each of the predetermined areas prepared by said first preparing means and for discriminating whether or not density of said frequency peak is a black side rather than a black side threshold value, and said correction reference value calculating means includes means for clearing density distribution data prepared by said first preparing means when density of said frequency peak is the black side rather than the black side threshold value.

3. The apparatus according to claim 1, wherein said discriminating means includes means for detecting a frequency peak of the density distribution of each of the predetermined areas prepared by said first preparing means so as to discriminate whether or not density of said frequency peak is a black side rather than a black side threshold value, and said correction reference value calculating means includes means for summing the frequencies around said density of said frequency peak when density of said frequency peak is the black side rather than said black side threshold value so as to clear the density distribution prepared by first preparing means when the summed value is larger than the predetermined value.

4. The apparatus according to claim 3, wherein said correction reference value calculating means includes means for summing the frequencies for a density width containing the density of said frequency peak when the density of said frequency peak is the black side rather than said black side threshold value so as to clean the density distribution prepared by first preparing means when the summed value is larger than the predetermined value.

5. The apparatus according to claim 3, wherein said discriminating means includes means for detecting a frequency peak of the density distribution of each of the predetermined areas prepared by said first preparing means so as to discriminate whether or not the density of said frequency peak is a black side rather than a black side threshold value and said frequency peak is a white side rather than a white side threshold value, and said correction reference value calculating means includes means for summing the frequencies around density of higher frequency peak when density of said frequency peak is the black side rather than said black side threshold value and is the white the side rather than said white side threshold so as to clear the density distribution prepared by first preparing means when the summed value is larger than the predetermined value.

6. An image forming apparatus comprising:
 a document plate on which a document is placed, the document plate having a plurality of reading areas;
 means for reading an image in the reading area in a main scanning direction as moving on said reading area of said document plate along a sub-scanning direction so as to output a pixel density signal every scanning line;
 means for preparing a 16 level density histogram for each scanning line from the density signal output from said reading means;
 means for discriminating that the scanning line is on the document from said histogram;
 means for clearing said histogram when said discriminating means discriminates that said scanning line is not on the document;
 first calculating means for accumulating the histograms by use of a weighting coefficient changing in accordance with number of scanning line counts of said sub-scanning direction when said reading means is moved along said sub-scanning direction, whereby preparing histograms accumulated up to a present line;
 second calculating means for calculating a density correction reference value for each of said scanning lines based on the histogram accumulated by said first calculating means;
 means for correcting the density signal by using the density correction reference value so as to output a corrected density signal; and
 means for forming an image on a image bearing member on the basis of the density signal.

7. The apparatus according to claim 6, wherein said discriminating means includes means for detecting a frequency peak of the histogram of each of said scanning lines prepared by said first preparing means so as to discriminate whether or not density of said frequency peak is a black side rather than a black side threshold value, and said clearing means includes means for clearing the histogram prepared by said first preparing means when density of said frequency peak is the black side rather than the black side threshold value.

8. The apparatus according to claim 6, wherein said discriminating means includes means for detecting a frequency peak of the histogram of each of said scanning lines prepared by said first preparing means so as to discriminate whether or not density of said frequency peak is a black side rather than a black side threshold value, and said clearing means includes means for summing the frequencies around density of said frequency peak when density of said frequency peak is the black side rather than said black side threshold value so as to clear the histogram prepared by first preparing means when the summed value is larger than a predetermined value.

9. The apparatus according to claim 8, wherein said clearing means includes means for summing the frequencies for a density width centrally containing the density of said frequency peak when the density of said frequency peak is the black side rather than said black side threshold value so as to clean the density distribution prepared by first preparing means when the summed value is larger than the predetermined value.

10. The apparatus according to claim 6, wherein said discriminating means includes means for detecting a frequency peak of the histogram of each of said scanning lines prepared by said first preparing means so as to discriminate whether or not a density of said frequency peak is a black side rather than a black side threshold value and said density is a white side rather than a wide side threshold value, and clearing means includes means for summing the frequencies around density of higher frequency peak when density of said frequency peak is the black side rather than said black side threshold value and is the white the side rather than said white side threshold so as to clear the histogram prepared by first preparing means when the summed value is larger than the predetermined value.

11. A method for forming an image, comprising the steps of:
 reading an image of a reading area of a document plate to output a density signal of each pixel, the document plate having a plurality of reading areas;
 preparing a first density distribution corresponding to each reading area based on the density signal;
 discriminating that the reading area corresponds to the document from the density distribution;
 clearing the density distribution when said reading area does not correspond to the document;
 accumulatively calculating said density distribution to prepare an accumulative density distribution;
 calculating a density correction reference value of each of said reading areas based on said accumulative density distribution;
 correcting said density signal obtained in said image reading step based on said density correction reference value so as to output a corrected density signal; and forming an image on a image bearing member on the basis of the corrected density signal.

12. An image forming apparatus comprising:

a document plate on which a document is placed, the document plate having a plurality of a reading areas;

means for scanning an image of the reading area of said document plate so as to output a density signal for each pixel;

means for preparing a density distribution based on the density signal;

means for calculating a density correction reference value of the density signal based on the density distribution prepared by said preparing means;

means for correcting the density signal by using the density correction reference value so as to output a corrected density signal;

means for forming an image on an image bearing member on the basis of the corrected density signal; and means for preventing an abnormal value from being calculated in the operation of the reference value calculation by said calculating means when the reading area corresponds to the area where no document is placed.

* * * * *